United States Patent [19]

Jones

[11] 4,432,234

[45] Feb. 21, 1984

[54] DETERMINATION OF PLASTIC ANISOTROPY IN SHEET MATERIAL

[75] Inventor: Alun Jones, Neath, Wales

[73] Assignee: British Steel Corporation, London, England

[21] Appl. No.: 341,571

[22] Filed: Jan. 21, 1982

[30] Foreign Application Priority Data

Jan. 23, 1981 [GB] United Kingdom ............... 8102185

[51] Int. Cl.³ .................................... G01N 29/00
[52] U.S. Cl. ................................. 73/597; 73/772
[58] Field of Search .............. 73/574, 579, 589, 597, 73/772, 87

[56] References Cited

U.S. PATENT DOCUMENTS 3,812,709 5/1974 Benson et al. .................. 73/597

OTHER PUBLICATIONS

R. T. Smith, "Stress-Induced Anistropy in Solids the Acousto-Elastic Effect," *Ultrasonics*, Jul.-Sep. 1963, pp. 135-147.

*Primary Examiner*—Stephen A. Kreitman
*Attorney, Agent, or Firm*—Bacon & Thomas

[57] ABSTRACT

This invention relates to a method of determining the average plastic strain ratio ($\bar{r}$) of sheet material of known density. This is effected by computation utilizing an empirical relationship existing for the material between $\bar{r}$ and an elastic property thereof, the elastic property being manifest as the velocity of mechanical vibrations propagated in the sheet.

9 Claims, 1 Drawing Figure

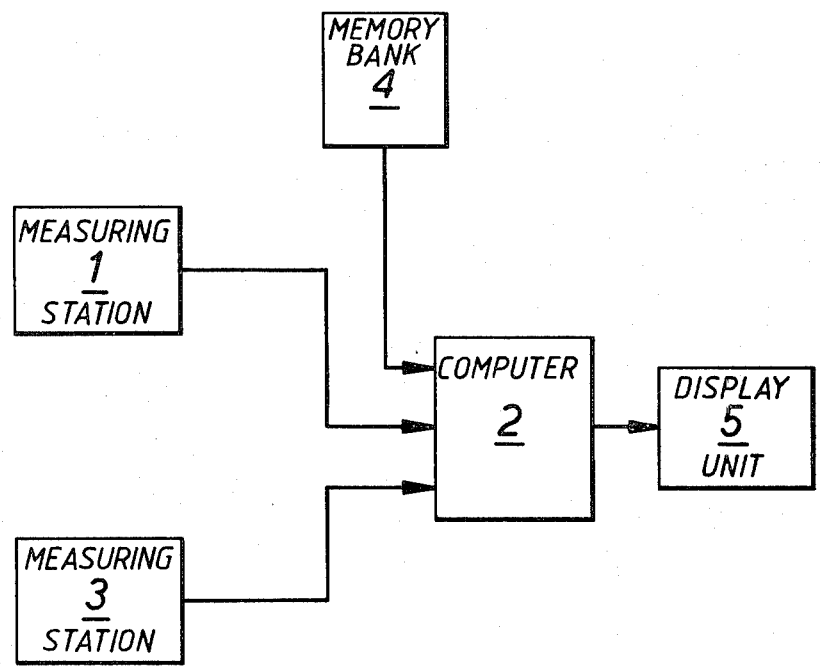

DETERMINATION OF PLASTIC ANISOTROPY IN SHEET MATERIAL

BACKGROUND OF THE INVENTION

This invention relates to the determination of plastic anisotropy in sheet materials and is particularly, though not exlusively, concerned with the rapid determination of the average plastic strain ratio ($\bar{r}$), of sheet material, which is an important factor in predicting its 'drawability' characteristics.

Hitherto, $\bar{r}$ has conventionally been determined by cutting three test specimens from a sheet and separately subjecting each to a tensile test, $\bar{r}$ then being determined from the relationship $$\bar{r} = \tfrac{1}{4}(r_0 + 2r_{45} + r_{90})$$

where:

the subscripts are the angles between the rolling direction and the axes of the specimens, and $\bar{r}$ is the ratio of the natural strains in the width and thickness directions due to tensile elongation.

Several disadvantages are associated with this method however. In particular the specimens must be carefully prepared to be accommodated in the testing machine and care is needed in setting up the machine, and, after straining, ascertaining the length and width strains with the required degree of accuracy. These procedures are time consuming and consequently efforts have recently been made to devise more rapid means for determining this drawability characteristic. Much work has centered on the automation of the tensile testing procedure, for example, by incorporating extensometers for simultaneously monitoring width and thickness strains, but the need for careful specimen preparation in the three different directions remains.

SUMMARY OF THE INVENTION

It is an object of this invention to provide an improved method of measuring the plastic properties of sheet material.

From one aspect the present invention provides a method of determining the average plastic strain ratio ($\bar{r}$) of sheet material of known density by computation utilising an empirical relationship existing for that material between $\bar{r}$ and an elastic property thereof, the elastic property being manifest as the velocity of mechanical vibrations which are propagated through the thickness of the sheet.

DETAILED DISCUSSION OF THE INVENTION

Conveniently, the vibrations may be in the longitudinal mode transmitted through the thickness of the sheet normal to the surface. Alternatively longitudinal, torsional or compound waves, e.g. Lamb waves, may be propagated in diverse directions through the material to determine the elastic property.

The elastic property may be a constant, e.g. Youngs Modulus (E)—the ratio of uniaxial stress to corresponding uniaxial strain—or the apparent Youngs Modulus $\Phi$ in a specified direction if the material is non-isotropic, and this may be determined by measuring the transit time (t/2) of a longitudinal mechanical vibration transmitted through the sheet thickness and independently measuring the sheet thickness (d) e.g. by physical means such as micrometer, by optical means, by nucleonic means, or indeed by any other means which is unaffected by variations in elastic anisotropy.

From the expression $$t = \frac{2 \times d}{V}$$

the elastic constant $\Phi$ may be derived since the velocity (V) is defined by $$V = \sqrt{\frac{\Phi}{\rho}}$$

where $\rho$ = density of material $\bar{r}$ is then determined from the previously established empirical relationship between $\Phi$ and $\bar{r}$.

It will be understood that the elastic modulus need not be expressly depicted as such, since this property is only inherently utilised in the determination of $\bar{r}$. Accordingly, in one practical embodiment a micrometer measurement is first made of the thickness of the sheet material, the value (d) of which is electronically stored and then the transit time (t) of an ultrasonic pulse transmitted through this material is likewise measured and stored. Also stored is the previously determined relationship between r for that material (measured conventionally) and the velocity of a longitudinal vibration through the material (V). The velocity V may thus be computed by a processor from the inputs specified, the appropriate value of $\bar{r}$ being retrieved directly from memory by comparing the computed value of V with the stored equivalent.

In another practical embodiment, only the 'thickness' quality of the sheet is utilised, the thickness being measured using a micrometer on one hand and by means of an ultrasonic thickness meter on the other; these measurements and the difference between the values (adjusted to a standard thickness of sheet) are electronically stored. Also stored is the previously determined relationship for that material between r (measured conventionally) and the difference (also for the standard thickness of sheet) between thickness readings measured by the two methods above. The $\bar{r}$ value of the sheet is then obtained directly by comparing the difference between the thickness readings with the stored equivalent.

BRIEF DESCRIPTION OF THE DRAWINGS

In order that the invention may be fully understood two embodiments thereof will now be described with reference to the accompanying drawings which is a schematic block circuit diagram of apparatus for determining $\bar{r}$ in accordance with this invention.

DETAILED DESCRIPTION OF THE DRAWINGS

Referring now to the drawing, measuring station 1 provides a digital signal (d) representative of a physical micrometer measurement of the thickness of a sample of sheet steel being assessed for drawability and the output from this unit is transmitted to and stored in a microprocessor based computer unit 2.

Measuring station 3 embodies an ultrasonic transmitter/receiver and a timer; this station functions by timing the interval between the launch and the return of a longitudinal pulse which travels through the thickness of the sample and is reflected back from its remote face.

The transmit time (t) of such a pulse through the material is represented by a digital output signal likewise transmitted to the computer unit 2. From these two signals is computed the velocity of the longitudinal pulse through the sample $V=2d/t$. The previously determined stored relationship between V and $\bar{r}$ measured conventionally for the material in question is then utilised to obtain the corresponding value of $\bar{r}$. In particular, the V, $\bar{r}$ relationship is conveniently stored in the form of a 'look up' table in memory bank 4. Alternatively $\bar{r}$ may be obtained by evaluating each time the empirical mathematical expression for $\bar{r}$ in terms of V and constants where these constants are stored as before. A combination of these two approaches is sometimes to be preferred.

The appropriate plastic strain ratio $\bar{r}$ is depicted directly on a display unit 5.

In an alternative embodiment the measuring station 1 again provides a signal representative of a physical micrometer measurement whilst the station 3 provides a signal also representative of thickness but in this instance measured ultrasonically. One example of such an ultrasonic thickness meter is Model No. CL 204 manufactured by Krautkramer. The two signals are fed to the computer unit 2, which in this instance operates to provide a measurement of the difference between these two signals adjusted to a standard thickness of sheet, e.g. 1 mm—since the 'measured' thickness difference will depend on the thickness of the sheet sampled. Memory bank 4 provides inputs representative of previously determined relationships for the various materials between $\bar{r}$ (measured conventionally) and the difference (for the standard sheet thickness) between thickness readings measured physically and ultrasonically as stated above. The $\bar{r}$ value of the actual sample selected is then obtained directly for display on the unit 5 by comparing the difference between the thickness readings as determined by the computer 2 with the stored equivalent from the memory bank.

Although this invention has been described with reference to the particular embodiments illustrated it will be understood that various modifications may be made without departing from the scope of this invention. For example, both measuring stations can be constituted by a single assembly, one or both of the micrometer anvils also serving as ultrasonic probes. Alternatively, another means may be used for the thickness measurement providing that it is unaffected by changes in elastic anisotropy, e.g. optical or ionising radiation means. Similarly, the ultrasonic probes may be of the non-contact variety, e.g. by utilising a suitable couplant. Furthermore, although the embodiments described involve measurements by the time-of-flight method, the invention would be equally applicable if measurements were made of the resonance frequency of the sample and a reference material, use being made in this instance of the relationship between resonance frequency and the velocity of propagation.

In addition, whilst this invention has been described with reference to a mild steel sample it is applicable wherever there exists a suitable relationship between drawability and elastic anisotropy, measurement being effected either off-line, as described, or on-line in a continuous system.

We claim:

1. A method of determining the average plastic strain ratio ($\bar{r}$) of sheet material of known density comprising: subjecting the sheet material to mechanical vibrations, determining an elastic property of the material which is manifest as the velocity of the mechanical vibrations which are propagated through the thickness of the sheet, and determining the value of r from a previously established empirical relationship between the said elastic property and $\bar{r}$.

2. A method as claimed in claim 1 further comprising the steps of:
   measuring the thickness of the sheet independently of the elastic property of the sheet material, transmitting ultrasonic pulses through the sheet, measuring the transit time of a transmitted pulse,
   determining therefrom a measurement of the thickness of the sheet, and determining the value of $\bar{r}$ from a previously established empirical relationship between the difference between the two measurements of sheet thickness and $\bar{r}$.

3. A method as claimed in claim 2 wherein signals representative of the measured and determined values of sheet thickness are transmitted to a micro-processor operable to standardise and compute the difference between the aforesaid measured and determined values of sheet thickness and to compare the computed difference with a previously derived stored empirical relationship between thickness difference and $\bar{r}$ as determined conventionally for the sheet material, whereby to provide a direct reading of $\bar{r}$.

4. A method as claimed in claim 1 further comprising the steps of:
   measuring the thickness (d) of the sheet independently of the elastic property of the sheet material, transmitting ultrasonic pulses through the sheet, measuring the transit time (t) of a transmitted pulse,
   determining the velocity (v) at which the pulse is transmitted through the sheet thickness from the values of d and t, and determining the value of $\bar{r}$ from a previously established empirical relationship between v and $\bar{r}$.

5. A method as claimed in claim 4 wherein signals representative of sheet thickness (d) and pulse velocity (V) are transmitted to a microprocessor operable to compare the determined value of V with a previously derived stored empirical relationship between pulse velocity and $\bar{r}$ as determined conventionally for sheet material, whereby to provide a direct reading of $\bar{r}$.

6. A method as claimed in claim 1 further comprising the steps of:
   subjecting said sheet material to mechanical vibrations,
   measuring the transit time (t/2) of a mechanical vibration transmitted through the sheet thickness,
   independently measuring the sheet thickness (d),
   determining the velocity (v) at which said mechanical vibration is transmitted through the sheet by the formula $$t = \frac{2 \times d}{V},$$

determining the elastic constant $\Phi$ from the formula $V = (\phi/\rho)$
   where $\rho$ is the density of the material,
   and determining the value of $\bar{r}$ from a previously established empirical relationship between $\Phi$ and $\bar{r}$.

7. A method as claimed in claim 1 wherein the sheet material is excited at its resonance frequency.

8. Apparatus for determining the average plastic strain ratio ($\bar{r}$) of sheet material, comprising a first station having means for propagating mechanical vibrations through the thickness of the sheet, a second station having means for measuring sheet thickness independently of the elastic property of the sheet material, computer means for processing the outputs from the first and second stations and comparing the processed output with stored values representative of $\bar{r}$ and predetermined by conventional means for that sheet material, and a display unit having means for providing a direct reading of $\bar{r}$ upon identity between said processed output and a said stored value.

9. Apparatus for determining the average plastic strain ratio ($\bar{r}$) of sheet material, comprising a measuring station having means for effecting a first measurement by propagating mechanical vibrations through the thickness of the sheet and means for effecting a second measurement independent of the elastic properties of the sheet material, computer means for processing the outputs from said station and comparing the processed output with stored values representative of $\bar{r}$ and predetermined by conventional means for that sheet material, and a display unit having means for providing a direct reading of $\bar{r}$ upon identity between said processed output and a said stored value.

* * * * *